United States Patent [19]

Moormann et al.

[11] 4,431,802
[45] Feb. 14, 1984

[54] N-HETEROCYCLYL-N-CYANO-N-(HETEROCYCLYTHIOALKYL)-GUANIDINES

[75] Inventors: Alan E. Moormann; Barnett S. Pitzele, both of Skokie; Gilbert W. Adelstein, Evanston; Nancy J. Malek, Skokie, all of Ill.

[73] Assignee: G. D. Searle & Co., Skokie, Ill.

[21] Appl. No.: 324,244

[22] Filed: Nov. 23, 1981

Related U.S. Application Data

[63] Continuation-in-part of Ser. No. 172,341, Dec. 16, 1980, abandoned, which is a continuation-in-part of Ser. No. 101,923, Dec. 16, 1980, Pat. No. 4,239,908.

[51] Int. Cl.³ ............................................. C07D 239/24
[52] U.S. Cl. ..................................................... 542/416
[58] Field of Search ......................................... 542/416

[56] References Cited

U.S. PATENT DOCUMENTS 4,239,769 12/1980 Price et al. ..................... 542/416
4,239,908 12/1980 Adelstein ........................ 542/416

FOREIGN PATENT DOCUMENTS 857388 2/1978 Belgium .
867594 11/1978 Belgium .

OTHER PUBLICATIONS

Gensler et al., J.A.C.S. vol. 77, p. 3262, 1955.
Meyers, J. Org. Chem. vol. 46, p. 3119, 1981.
Plevyak et al., J. Org. Chem. vol. 44, p. 4078, 1979.

Primary Examiner—Jane T. Fan
Attorney, Agent, or Firm—James G. Passe

[57] ABSTRACT

Compounds of formula I and salts thereof which are orally pharmacologically active as inhibitors of gastric secretion are disclosed.

5 Claims, No Drawings

N-HETEROCYCLYL-N-CYANO-N-(HETEROCYCLYTHIOALKYL)-GUANIDINES

This application is a continuation-in-part of application Ser. No. 172,341, filed 12/16/80 now abandoned which is a continuation-in-part of Ser. No. 101,923 filed 12/16/80 now U.S. Pat. No. 4,239,908.

BACKGROUND OF THE INVENTION

The present invention relates to orally pharmacologically active N-heterocyclyl-N'-cyano-N"-(heterocyclylthioalkyl)-guanidine of formula I and pharmacologically acceptable salts thereof.

A number of quanidines have previously been described that act as inhibitors of gastric secretion. Of importance is U.S. Pat. No. 4,239,908 which describes N-aralkenyl-N'cyano-N"-(heterocyclythioalkyl)-guanidines. The present invention is of importance because of the unexpectedly high oral activity when compared to previous guanidines of this type.

SUMMARY OF THE INVENTION

What is specifically described is a compound of formula I:

$$A(CH_2)_dS(CH_2)_eNHCNHCH_2CH=CH-Het \quad (I)$$
$$\underset{NCN}{\|}$$

In formula I, A is an imidazolyl, oxazolyl, thiazolyl or furyl radical of the formulas II, III, or IV.

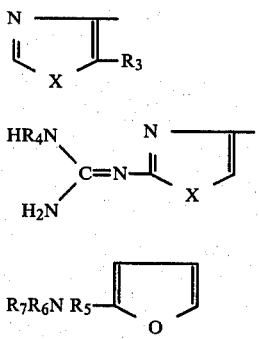

In formula I, Het is a pyridinyl, pyrimidinyl, pyrazinyl, pyridazinyl, thiophenyl, furanyl, pyrrolyl, pyrazolyl, or thiazolyl radical of the formulas V, VI, VII, VIII, IX, X, Xa, Xb, or Xc.

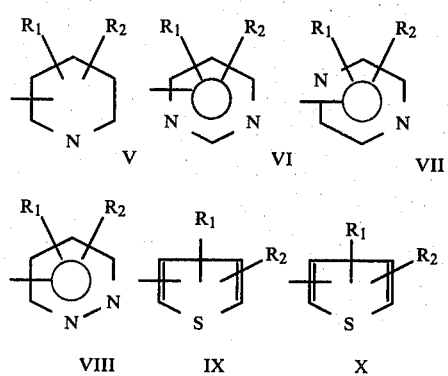

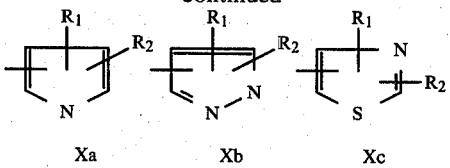

$R_1$ and $R_2$ may be the same or different and each represents hydrogen, halogen, hydroxy, trifluoromethyl or straight-chain or branched-chain alkoxy containing 1 to 7 carbon atoms and either unsubstituted or substituted by aryl or cycloalkyl. In addition, $R_1$ and/or $R_2$ can represent an amino radical either unsubstituted or substituted with at least one acyl radical or straight-chain or branched-chain alkyl radical, each containing 1 to 7 carbon atoms, and the alkyl radical being either unsubstituted or substituted by aryl or cycloalkyl. In the alternative, $R_1$ and $R_2$ can be interconnected forming a group having terminal oxygen atoms which are separated by a methylene or ethylene radical and which are attached to adjacent carbon atoms on the phenyl ring in formula I.

In formulas II and III, X represents -O-,-S-, or -NH-. In addition, in formula II, $R_3$ represents hydrogen, halogen or straight-chain or branched-chain alkyl containing 1 to 7 carbon atoms. When X in formula III represents S or NH, $R_4$ represents hydrogen or straight-chain or branched-chain alkyl containing 1 to 7 carbon atoms. When X in formula III represents O, $R_4$ is hydrogen.

In formula IV, $R_5$, is a straight or branched alkylene chain of 1 to 6 carbon atoms, and $R_6$ and $R_7$ can be the same or different and each represents hydrogen, cycloalkyl or straight or branched-chain alkyl unsubstituted or substituted by aryl, each containing 1 to 7 carbon atoms.

In the alternative, $R_6$ and $R_7$ can be interconnected and can contain oxygen, as tetramethylene, pentamethylene, methyleneoxyethylene, methyleneoxytrimethylene or ethyleneoxyethylene, to form together with the nitrogen atom in formula III a 5- or 6-membered heterocyclic ring.

In formula I, when A is of formula II or IV, d is 0,1 or 2 and e is 2 or 3. When A is of formula III and X represents S or NH, d is 1 or 2 and e is 2 or 3. When A is of formula III and X is O, d is 1 and e is 2. In all cases, the sum of e and d is 3 or 4.

Haolgen radicals suitable as $R_1$, $R_2$ and $R_3$ include fluorine, chlorine, bromine and iodine. Alkoxy radicals suitable as $R_1$ and $R_2$ include methoxy, ethoxy, cyclohexylmethoxy, phenylmethoxy and n-propoxy, n-butoxy, n-hexoxy and n-heptoxy and their branched-chain isomers. Alkyl radicals suitable as $R_3$, $R_4$, $R_6$ and $R_7$ and as substituents in the amino radicals of $R_1$ and $R_2$ include methyl, ethyl, n-propyl, n-butyl, n-pentyl, n-hexyl and n-heptyl and their branched-chain isomers, as well as phenylmethyl and cyclohexylmethyl. Additional alkyls suitable as substituents on the amino of $R_1$ and $R_2$ are phenylmethyl, cyclohexylmethyl, cyclopentylmethyl and cyclopentylethyl. Additional alkyls suitable as $R_6$ and $R_7$ include cyclopentyl, cyclohexyl and phenylmethyl. Acyl radicals suitable as substituents in the amino radicals of $R_1$ and $R_2$ include acetyl, propionyl, butyryl, valeryl, caproyl, enanthyl, and benzoyl.

Preferably in formula I, d is 1, and/or e is 2, and/or the sum of d and e is 3. It is also preferred that $R_1$ and/or $R_2$ is hydrogen, hydroxy, halogen, methoxy, phenylmethoxy or amino substituted with acetyl, methyl or phenylmethyl, and more preferably is mono-substituted, or alternatively that $R_1$ and $R_2$ are interconnected with the oxygen atoms therein separated by a methylene radical.

Preferably in formulas II and IV, X is NH and A is imidazolyl. It is also preferred that $R_3$ in formula II is hydrogen or methyl and that $R_4$ in formula III is hydrogen or methyl. $R_5$ in formula IV is preferably methylene. Also in preferred embodiments, $R_6$ and/or $R_7$ in formula IV is hydrogen or methyl-more preferably one of $R_6$ and $R_7$ is methyl and the other is hydrogen and most preferably both are methyl or alternatively $R_6$ and $R_7$ are interconnected as tetramethylene or pentamethylene.

The novel compounds of the present invention are useful by reason of their valuable pharmacological properties as is exemplified by their ability to inhibit the gastric secretion stimulated by secretogogues such as histamine and pentagastrin while furthermore possessing the surprising advantages of lacking the potent undesirable side effects displayed by related substances.

One specific assay used to detect gastric antisecretory activity is described as follows. Adult female beagle dogs weighing 13–25 kilograms are prepared with denervated fundic Heidenhain pouches. After a recovery period of at least 4 weeks following surgery, the animals are fasted for approximately 20 hours, then are placed in Pavlov stands and infused intravenously with saline solution. The pouched secretions are collected every 15 minutes and measured for volume and total acidity by titration with 0.1 N sodium hydroxide to pH 7.0. Following a 30 minute basal secretion the dogs are infused with a saline solution of histamine dihydrochloride at a dose of 1.0 mg./hr. The volume of the diffusion is kept at approximately 13 ml./hr. A steady state plateau of gastric secretion is obtained approximately 1 hour following the start of histamine infusion at the end of which time the test compound dissolved in a solution of 30 percent by volume of propylene gycol and 20 percent by volume of ethanol in water is administered by a single intravenous injection bolus. The duration of the anti-secretory effects is determined and the side effects if any, recorded. The compound is rated active if significant inhibition of secretory parameters occurs following compound treatment.

A second specific assay used to detect gastric antisecretory activity is described as follows. Adult female beagle dogs weighing 7–10 kilograms are prepared with Thomas-type gastric fistulas. After a recovery period of at least 4 weeks following surgery, the animals are fasted for approximately 20 hours, then are placed in Pavlov stands and infused intravenously with saline solution. The gastric secretions are collected every 15 minutes and measured for volume and total acidity by titration with 0.1 N sodium hydroxide to pH 7.0. Following a 30 minute basal secretion the dogs are infused with a saline solution of histamine dihydrochloride at a dose of 1.0 mg./hr. The volume of the diffusion is kept at approximately 6.5 ml./hr. A steady state plateau of gastric secretion is obtained approximately 1 hour following the start of histamine infusion, at the end of which time the test compound dissolved in a solution of 30 percent by volume of propylene glycol and 20 percent by volume of propylene glycol and 20 percent by volume of ethanol in water is administered intragastrically through a gastric dosage plug. The gastric cannula is then closed to allow sufficient contact time between the test compound and the gastric mucosa. After 30 minutes of contact time passes, the gastric cannula is opened and internal gastric secretion collections are taken. The duration of the anti-secretory effects is determined and the side effects, if any, recorded. The compounds is rated active if statistically significant inhibition of secretory parameters occur following compound treatment.

A preferred compound of this invention N-cyano-N'-[2-(((5-methyl-1H-imidazol-4-yl)methyl)thio)ethyl]-N''-[5-(2-aminopyrimidinyl) 2-propen-1-yl] guanidine which was found to inhibit gastric secretions in both foregoing tests. Suitable dosages are in the range of 0.5 to 10 mg./kg/day when administered as hereinafore described.

The distinguishing response in dogs set forth above is of course intended merely to illustrate this aspect of the instant invention, and accordingly is not to be construed as either delimiting or exclusionary. Appropriate dosages in any given instance, of course, depend upon the nature and severity of the condition treated, the route of administration, and the species of mammal involved, including its size and any individual idiosyncrasies which obtain.

For therapeutic purposes, the compounds of this invention are ordinarily combined with one or more adjuvants appropriate to the indicated route of administration. If per os, they may be admixed with lactose, sucrose, starch powder, cellulose esters of alkanoic acids, cellulose alkyl ethers, talc, stearic acid, magnesium stearate, magnesium oxide, sodium and calcium salts of phosphoric and sulfuric acids, gelatin, acacia, sodium alginate, polyvinylpyrrolidone, and/or polyvinyl alcohol, and thus tableted or encapsulated for convenient administration; alternatively, they may be dissolved or suspended in water or a comparably innoculous liquid. Parenteral administration may be effected via sterile fluid admixture with water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art; see, for example, F. W. Martin et al., "Remington's Pharmaceutical Sciences," 14 Ed., Mack Publishing Company, Eaton, Pa., 1965.

Compounds of formula I when d is 1 or 2 can be prepared by a process involving reacting a heterocyclylalkylthioalkylamine of formula XI and dimethyl N-cyano-dithioimidocarbonate, preferably in equimolar amounts, at room temperature in a protic or aprotic polar solvent such as an alcohol, acetonitrile, dimethylformamide or a water-alcohol mixture, to form an isothiourea of formula XII.

A(CH$_2$)$_d$S(CH$_2$)$_e$NH$_2$  XI

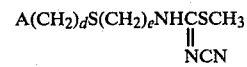

The isothiourea of formula XII is solidified by removal of solvent or by precipitation induced by the addition of water to the solvent. The isothiourea then is reacted with a heteroallylamine of formula XIII, preferably two molecular equivalents, at elevated temperatures in the range of about 90° C. to about 150° C., to form a product of formula I. Preferably the excess amine of formula XIII acts as the solvent, but a protic or aprotic polar solvent may be used in this step.

Het—CH=CH—CH$_2$NH$_2$     XIII

Alternatively the heteroallylamine of formula XII is reacted with dimethyl N-cyanoimidodithiocarbonate at room temperature in a protic or aprotic polar solvent such as an alcohol, acetonitrile, dimethylformamide or a water-alcohol mixture, to form an isothiourea of formula XIV which after separation in solid form as described above, is then reacted with a heterocyclylalkylthioalkylamine, of formula XI at elevated temperatures in the range of about 90° C. to about 150° C. to form a product of formula I.

Het-CH=CH—CH$_2$NH—C(SCH$_3$)=N—C≡N     XIV

Preferably the excess amine of formula XI acts as the solvent, but the protic or aprotic solvents noted above may be used in this alternative procedure.

In formulas XI-XIV, A,d,e,Het,R$_1$ and R$_2$ are defined in formulas I-X.

Compounds of formula I when d is 0 can be prepared by a process involving reacting a heterocyclylthiol of formula IX with an N-ω-bromoalkylphthalimide of formula X in alkaline methanol to form the alkylate of formula XI which is then reacted in ethanol with hydrazine to form a product of formula XII.

A—SH     XV

Br(CH$_2$)$_e$—N(phthalimide)     XVI

A—S—(CH$_2$)$_e$—N(phthalimide)     XVII

A—S—(CH$_2$)$_e$—NH$_2$     XVIII

In formulas XV–XVIII A and e are as defined in formula I. The heterocyclylthioalkylamine of formula XVIII is then reacted with a material of formula XIV to form a product of formula I wherein d is 0.

Compounds of formula XIII can be readily prepared by a process involving reacting a halide of formula XIX, wherein Het is as defined in formula I and preferably halide is iodide or bromide with, with N-allyl phthalimide in the presence of Palladium acetate to form an unsaturated phthalimide of formula XX, as reportted in Heck J. Org. Chem. 44, p. 4078 (1979).

Het-halide     XIX

Het—C(=O)H     XIXa

Het-CH=CHCH$_2$—N(phthalimide)     XX

This unsaturated phthalimide is reacted with hydrazine to form a product of formula XIII, as reported in Gensler and Rockett, J.A.C.S. 77, p. 3262 (1955).

Additionally unsaturated phthalimides of structure XX, wherein Het is as defined in formula I, may be prepared by a process involving reacting an aldehyde of structure XIXa, with vinyl tri-n-butyl-phosphonium salts and sodiophthalimide, and hydrolysis of the product having structure XX with hydrazine to form a product of formula XII, as reported in A. I. Meyers, J. Org. Chem. 46, p. 3119 (1981).

DESCRIPTION OF THE PREFERRED EMBODIMENTS

The present invention will be more clearly understood from the following specific examples. The following examples describe in detail compounds illustrative of the present invention and methods which have been used for their preparation.

EXAMPLE I 16.39 (0.1 mole) 2-bromothiophene, 19.4 (0.104 mole) allyl phthalimide, 28 ml. (0.2 mole) Et$_3$N, 224 mg. (0.001) mole Pd(OAc)$_2$, and 608 mg. triorthotolyl phosphine were placed in a glass bomb and purged with N$_2$. The bomb was sealed and heated to 100° C. for 18 hours.

After washing the residue with H$_2$O, an oil was obtained, which was dissolved in methylene chloride, the insoluble material filtered and then dried over M$_g$SO$_4$. The solvent was removed *in vacuo* and the residue crystallized from Et$_2$O/MeOH. Yield 5.8 g of product of formula XXI.

C$_{15}$H$_{11}$NO$_2$S Cal C: 66.90, H: 4.12, N: 5.20, S: 11.90, 269.32, Found C: 66.70, H: 4.07, N: 5.26, S: 11.59.

NMR(CDCl$_3$) dδ4.4 (2H); mδ6.3–5.8 (1H), mδ7.4–6.5 (4H); mδ8.0–7.6 (5H).

XXI

EXAMPLE 2

5.0 (0.018 mole) of the above phthalimide 0.92 g (0.018 mole) hydrazine hydrate, and 50 ml ethanol were refluxed and the reaction followed by tlc. The reaction mixture was cooled the solid filtered and washed with ethanol. The solid was dried and the amine freed from the salt comples by dissolving the amine in 5 percent NaOH extracting the amine into Et$_2$O 2×100 ml. The Et₂O layer was dried over MgSO₄ and the solvent was removed in vacuo. Yield 2.1 g of a product of formula XXII.

NMR (CDCl₃)+D₂O_x s δ1.33 (2H exchangable); d δ3.4 (2H); m δ6.7–5.8 (2 H); m δ7.3–6.7 (3H).

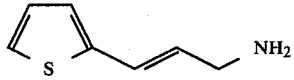
XXII

EXAMPLE 3

2.1 g (0.015 mole) of the above amine and 2.1 g (0.008 mole) mg of the isothiourea of formula XXIII were combined and heated in an oil bath at 100° C. for 4 hours. The residue was chromatographed on silica gel using MeOh/CH₂Cl₂ with a constant 0.1 percent NH₄OH. The fractions containing the product were combined the solvent removed in vacuo and the residue recrystallized from MeOH/Et₂O. Yield 1.7 g of a product of formula XXIV.

C₁₆H₂₀N₆S₂ Calc C: 50.77, H: 5.86, N: 22.20, S: 16.94, H₂O 378.50, Found C: 51.01 H: 5.77 N: 22.10 S: 16.88

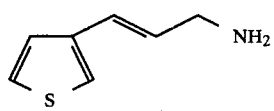
XXIII

NMR (DMSO)+D₂O_x s δ2.15(3H); m δ2.6 (2H); m δ3.35(2H) s δ3.95(2H); mδ7.9–5.8 (6H) 3 exchangeable
IR (KBr) 2169 cm⁻¹

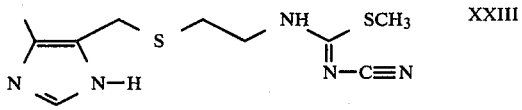
XXIV

EXAMPLE 4

25.0 g (0.15 mole) 3-bromothiophene, 29.7 g (0.15 mole) allylphthalimide, 43 ml (0.3 mole) Et₃N, 345 mg (0.0015 mole) Pd(OAc)₂, and 935 mg (0.003 mole) triorthotolylphospine were reacted and worked up as in Example 1.

Yield 23.3 g of a product of formula XXV.

C₁₅H₁₁NO₂S Calc C: 66.90, H: 4.12, N: 5.20, S: 11.90, 269.32, Found C: 66.50, H: 4.07, N: 5.27, S: 11.89.

NMR(CDCl₃) d δ4.3 (2H); m δ6.9–5.7 (2H), s δ7.1 (3H); m δ7.9–7.5 (4H).

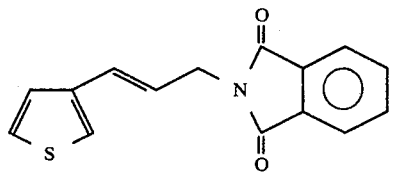
XXV

EXAMPLE 5

10.0 g (0.032 mole) of the above phthalimide and 1.84 g (0.032 mole) hydrazine hydrate in 100 ml EtOH were reacted as in Example 2. Yield 4.3g of a product of formula XXVI NMR (CDCl₃)+D₂O_x s δ1.2 (2H exchangable); d δ3.4 (2H); m δ6.5–5.8 (2H); m δ7.3–6.9 (3H).

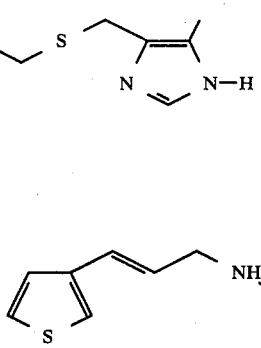
XXVI

EXAMPLE 6

2.1 (0.015 mole) of the above amine and 2.1g (0.008 mole) of cimetidineisothiourea (XXIII) were reacted at 95° C. as in Example 3. Yield 1.9g of a product of formula XXVII.

C₁₆H₂₀N₆S₂H₂0 Calc C: 50.77 H: 5.86 N:22.20 S: 16.94 378.50 Found C: 50.84 H: 5.89 N: 16.66.

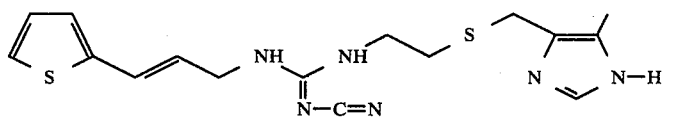
XXVII 2.1g (0.015 mole) of the amine produced in Example 5 and 2.6g (0.008 mole) of isothiourea of structure of formula XXVII were reacted at 95° C. as Example 3. Yield 1.27g of a product of formula XXIX.

C₁₆H₂₀N₈S₃ Calc C: 45.69, H: 4.79, N: 26.64, S:22.87, 420.57 Found C: 45.83, H: 4.76, N: 26.48, S: 22.66.

NMR (DMSO) m δ2.9–2.3 (2H); m 4.2–3.0 (6H) m δ7.7–5.7 (6H)
IR (KBr) 2160cm⁻¹

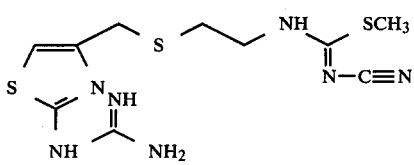
XXVIII

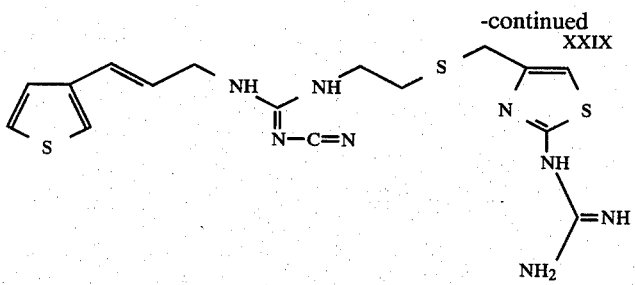

31.7g (0.2 mole) 5-bromopyrimide, 37.4g (0.2 mole) allylphthalimide, 448 mg (0.002 mole) Pd(OAc)₂, 1.2g (0.004 mole) triorthotolylphosphine and 56 ml (0.4 mole) Et₃N reacted as in Example 1. Recrystallized from DMF. Yield 34.0g of product of formula XXX.

$C_{15}H_{11}N_3O_2$ Calc C: 67.92 H: 4.18 N: 15.84, 265.26, Found C: 67.79, H: 4.03 N: 1583.

NMR (DMSO) d δ4.4 (2H); m δ(6.57 (2H); s δ 7.86 (4H) s δ 8.85(2H); s δ 9.0 (1H)

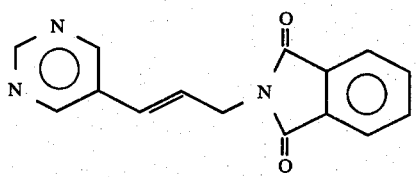

EXAMPLE 9

13.2g (0.05 mole) of the above phthalimide and 2.5 (0.05 mole) hydrazine hydrate in 25 ml EtOH were reacted as im Example 2. Yield 2.4g of a product of formula XXXI.

NMR (CDCl₃ and DMSO) and D₂Oₓ d δ 6.6 (2H) s δ 8.88 (2H); s δ 9.06 (1H)

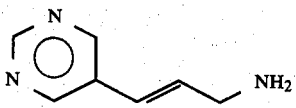

EXAMPLE 10

5.8g (0.0429 mole) of the above amine and 8.5g (0.032 mole) cimetidineisothiourea were reacted at 100° C. as in Example 3.

Yield 2.2g of a product of formula XXXII. $C_{16}H_{20}N_8S.\frac{1}{2}$

Et₂O.⅛H₂CO₃ Calc C: 54.25 H: 6.34, N: 27.92, S: 7.99, 401.25, Found C: 54.09, H: 5.98, N: 27.54, S: 8.32.

NMR(DMSO)+D₂Oₓ s δ 2.11 (3H); m δ 2.85-24 (2H), zm δ 3.55-3.15 (2H); s δ 3.65 (2H); m δ 4.17-3.85 (2H) m δ 6.55 (2H); s δ7.45 (1H); s δ 8.88 (2H); s δ 9.11 (1H). (3H) exchangable IR (KBr) 2175cm⁻¹

EXAMPLE 11

8.7g (0.05 mole) 2-amino-5-bromopyrimidine and 9.4g (0.05 mole) allylphthalimide, 112mg (0.0005 mole) Pd(OAc)₂, and 304mg (0.001 mole) triorthotolylphosphine in 14ml (0.1 mole) Et₃N reacted as in Example 1. Yield 6.0g of a product of formula XXXIII.

$C_{15}H_{12}N_4O_2.\frac{1}{4}H_2O$ Calc C: 63.26, H: 4.42, N: 19.67, 284.78, Found C: 63.47, H: 4.37, N: 19.55.

NMR(DMSO)+D₂Oₓ s δ 2.8 (2H exchangable); d δ 4.3 (2H) m δ 6.3 (2H); s δ 6.67 (2H exchangable); s δ 7.85 (4H) s δ 8.3 (2H)

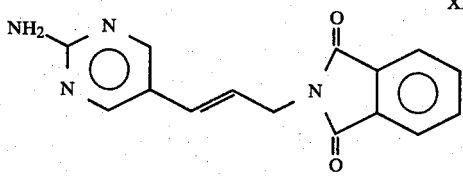

EXAMPLE 12

19.3g (0.068 mole) of the above phthalimide and 3.4g (0.068 mole) hydrazine hydrate in 200ml EtOH reacted as in Example 2. An overnight continuous extraction using methylene chloride was used to extract the product from the aqueous layer. Yield 4.5g of a product of formula XXXIII.

NMR (D₂O) d δ 3.45 (2H); m δ (2H); s δ 8.3 (2H).

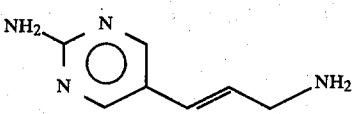

EXAMPLE 13

4.5g (0.03 mole) of the above amine and 4.0g (0.015 mole) of cimetidineisothiourea reacted at 110° C. as in Example 3. Yield 524.6 mg of a product of formula XXXIV.

$C_{16}H_{21}N_9S$ Calcs: 49.42, H:6.16, N: 31.44, S:7.99, 0.3MH₂O.½MeOH Found C: 49.25, H:5.80, N:31.71, S:7.97, NMR (MeOD) s δ 2.18.3(H); t δ 2.75 (2H); m δ 3.5-3.2 (2H); s δ 3.7 (2H); d δ 4.0 (2H); m δ 6.4–6.25 (2H) s δ 7.5 (1H); s δ 8.33 (2H).

IR (KBr) 2155 cm⁻¹

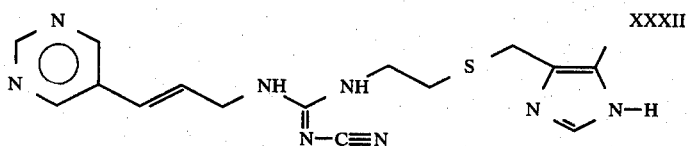

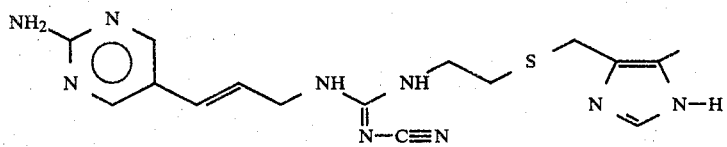

XXXIV

EXAMPLE 14

87.7g (0.436 mole) 3-iodopyridine, 80.14 g (0.428 mole) allylphthalimide, 0.8g (0.0042 mole) Pd(OAc)$_2$ and 67.5 (0.482 mole) Et$_3$N in 72.3 ml acetonitrile reacted as in example 1. Recrystallized from diethylether. Yield 80g of a product of formula XXXV

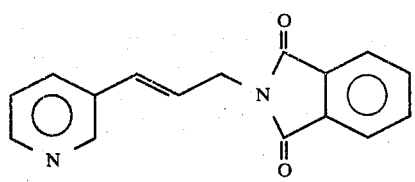

XXXV

EXAMPLE 15

85.3g (0.33 mole) of the above phthalimide and ≃ml (0.516 mole) hydrazine hydrate in 1.0 liter of ethanol is reacted as in example 2. The pH is adjusted to 5 with con HCl anf filtered and solid and washed with methanol. Yield 63.3g of a product of formula XXXVI.

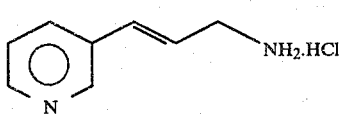

XXXVI

EXAMPLE 16

50g (0.29 mole) of the above amine hydrochloride is neutralized in ethanol with 20.2g (0.29 mole) 80 percent KOH pellets. The white solid, (KCl) is filtered from the solution of the amine.

To the filtrate is added 42.8 g 0.29 mole) dimethyl-N-cyanoimidodithiocarbonate and stirred over night at room temperature. The resulting solid is filtered and washed with ethanol and dried. Yield 26.39 of a product of formula XXXVII.

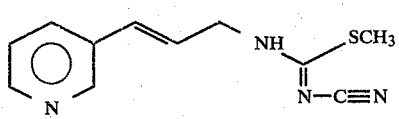

XXXVII

EXAMPLE 17

20.2g (0.08 mole) of an imidazole of formula XXXVIII is neutralized with 10.2g (0.18 mole) KOH in ethanol. The solid KCl is removed through filtration and the solvent removed in vacuo to yield the free base of the imidazone of formula XXXVIII. 0.17g (.0075 mole) sodium metal is dissolved in 2 ml of methanol to which 0.97 ml (0.0094 mole) thiophenol is added and the solvent removed in vacuo to yield sodium thiophenoate. 17.5g (0.075 mole) pyridyl isothiourea of formula XXXVII, the free base of formula XXXVIII and the sodium thiophenoate are heated at 70° C. in 200 ml of acetonitrile until tlc indicated the isothiourea is consumed. The solvent was removed in vacuo and the residue chromatographed on silica eluting with a mixture of ethanol/methylene chloride/ammonium hydroxide. The second major component is collected and further purified through reverse phase chromatography eluting with MeOH/H$_2$0. Yield 4.9g of a product of formula XXXIX.

C$_{17}$H$_{21}$N$_7$S.H$_2$O  Calc C:54.67, H:6.21, N:26.25, S:8.58, Found C:54.85 H:5.89 N:26.02 S:8.70.

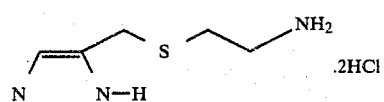

XXXVIII

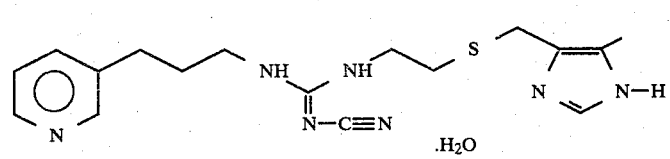

XXXIX

EXAMPLE 18

The compound of structure XL is prepared as reported by A. I. Meyers et al J. Org Chem 46, p. 3119 (1981).

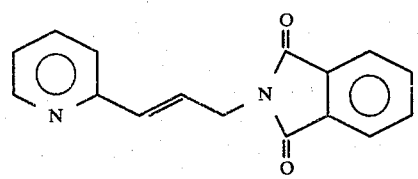

XL

EXAMPLE 19

3 g (0.011 mole) of the above phthalimide and 0.6ml (0.012 mole) hydrazine hydrate in 100 ml of ethanol are reacted as in Example 2. The solid is used before treating with sodium hydroxide to react with an equimolar amount of dimethyl-N-cyanoimido-dithiocarbonate as in example 16. Yield 0.62g of a product of formula XLI.

thio)ethyl]-N-cyano-N''-[4-bromo-1-thiophenyl-2-propen-1-yl]guanidine represented by the formula

XLI

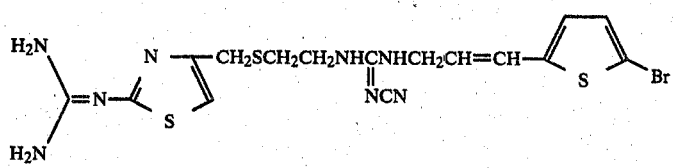

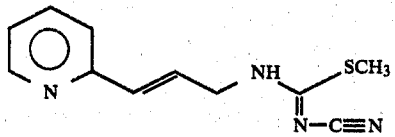

EXAMPLE 20

In a manner as described previously, the imidazole methylthioethylamine (12.6 g, 0.074 mole), furanyl propenylcarbamimidothioic acid methyl ester (15 g, 0.068 mole), thiophenol (2.32 ml, 0.22 mole) and sodium methoxide (from 0.51 g of sodium in 7 ml of methanol) were mixed, and the mixture was refluxed overnight under a nitrogen atmosphere. The mixture was cooled, filtered and stripped, and the oily residue chromatographed over silica gel eluting with 5 percent methanol-methylene chloride.

N-cyano-N'-[2-((5-methyl-1H-imidazol-4-yl)methyl)-thioethyl]-N''-[3-(2-furanyl)-2-propen-1-yl]guanidine was obtained as an oil, which was dried at 45° under high vacuum to give analytically pure material having the formula:

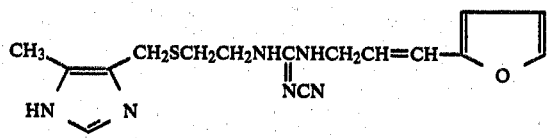

EXAMPLE 21

A solution of 2-bromo-5(3-aminopropen-1-yl)thiophene hydrochloride (25.5 g, 0.1 mole) in ethanol (200 ml) was slurried with potassium hydroxide (6.0 g, 0.1 mole) and the organic salts were filtered. To the filtrate was added dimethyl N-cyanoimidodithiocarbonate (14.6 g, 0.1 mole) and the mixture was stirred overnight at room temperature. Evaporation of the solvent and slurring with water gave the isothiourea. A mixture of isothiourea (15.8 g, 0.05 mole) and guanidinothiazolylmethylthioethylamine (11.6 g, 0.05 mole) in acetonitrile (200 ml) was refluxed for 3 days. The solution was stripped, the residue taken up in 10 percent methyl alcohol/methylene chloride and chromatographed on silica with the same solvent to yield N'-[2-(((2-amino(-dimethylamino) methylene)amino-thiazol-4-yl)methyl)-

EXAMPLE 22

Following the method of Example 21, a mixture of N-cyano-S-methyl-N'-2-pyrrolylpropenyl isothiorea(22.0g, 0.1 mole) and methylimidazolylmethylthioethylamine (17.0 g, 0.1 mole) was refluxed in acetonitrile (200 ml) for 5 days. The mixture was cooled, the solvent stripped, the residue taken up in 10 percent methanol-methylene chloride and chromatographed on silica gel to afford N-cyano-N'[(5-methyl-1H-imidazol-4-yl)methyl]thioethyl-N'-3(2-pyrrolidyl-2-propen-1-yl]guanidine as a residue having the structure

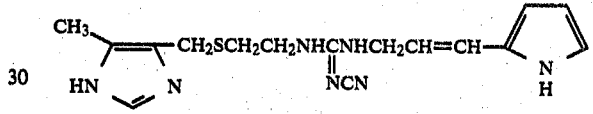

EXAMPLE 24

Following the method of Example 21, a mixture of N-cyano-S-methyl-N'-(3,5-dimethyl-4-pyrazolyl)propenyl isothiourea (29.7 g, 0.1 mole) and dimethylaminofurylmethylthioethylamine (20.3 g, 0.1 mole) in acetonitrile (200 ml) was refluxed for 4 days under a nitrogen atmosphere. The solution was stripped, the residue taken up in 4 percent methanol/methylene chloride and chromatographed on silica gel with the same solvent, and the product, N-cyano-N'-2-[4-dimethylaminomethylfuryl)methylthioethyl-N''-(3,5-dimethyl-4-pyrazolyl)-2-propen-1-yl]guanidine, was isolated as a residue with the following formula;

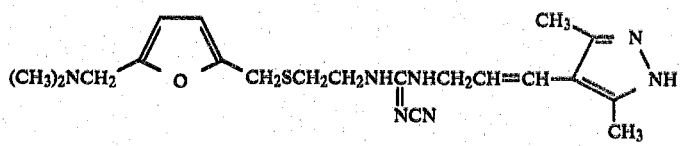

EXAMPLE 25

Following the method of Example 21, a mixture of N-cyano-S-methyl-N'-(4-pyridyl)-1-propenylisothiourea(23.3 g, 0.1 mole) and methylimidazolylmethylthioethylamine (17.0 g, 0.1 mole) in acetonitrile (200 ml) was refluxed for 4 days. The solution was stripped, the residue taken up in 10 percent methanol-methylene chloride and chromatographed on silica gel with the same solvent to afford the product, N-cyano-N'-2-[(5-methyl-1H-imidazol-4-yl)methyl]-thioethyl-N'''-[4 pyridinyl-2-propen-1-yl]guanidine, as a residue with the formula

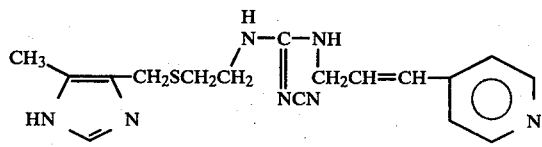

EXAMPLE 26

Following the method of Example 21, a mixture of N-cyano-5-methyl-N'-(2-thiazolyl)-propenylsothiourea (23.8 g, 0.1 mole) and guanidinothiazolylmethylthioethylamine (2.3g, 0.1 mole) in acetonitrile (200 ml) was refluxed for 5 days. The solvent was stripped and the residue taken up in 10 percent methanol-methylene chloride. Chromatography on silica gel with the same solvent system resulted in a product having the following formula:

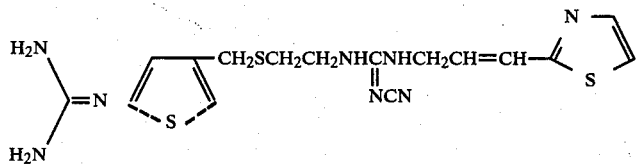

From the above description, it is apparent that the objects of the present invention have been achieved. While only certain embodiments have been set forth, it will be apparent to those skilled in the art that many modifications, both of materials and methods, may be practiced without departing from the purpose and intent of this disclosure.

Having decribed the invention, what is claimed is:

1. A compound of the formula:

or a pharmacologically acceptable salt thereof wherein Het is of the formula:

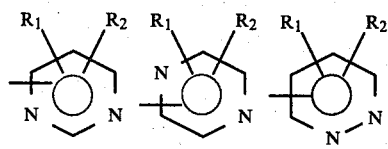

wherein A is of the formula:

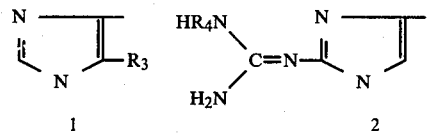

wherein
R$_1$ and R$_2$ can be the same or different and each represents hydrogen, halogen, hydroxy, trifluoromethyl, alkoxy containing 1 to 7 carbon atoms
R$_3$ represents hydrogen, halogen or alkyl containing 1 to 7 carbon atoms;
R$_4$ represents hydrogen or alkyl containing 1 to 7 carbon atoms d is 0. 1 or 2 and e is 2 or 3 when A is of formula and d is 1 or 2 and e is 2 or 3 when A is of formula 2.

2. A compound according to claim 1 wherein A is

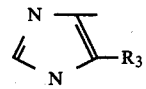

3. A compound according to claim 2 wherein Het is:

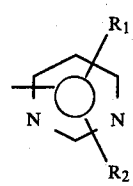

4. N-cyano-N'-[2-(((5-methyl-1H-imidazol-4-yl)methyl)(thio)ethyl]-N''-[3-(5-(2-aminopyrimidinyl)) 2-propen- 1-yl] guanidine or pharmaceutically acceptable salt thereof.

5. N-cyano-N'[2-(((5-methyl-1H-imidazol-4-yl)methyl)thio)ethyl]-N''-[3-(5-pyrimidinyl)-2-propen-1-yl]guanidine or a pharmaceutically acceptable salt thereof.

* * * * *